United States Patent [19]
Arai

[11] Patent Number: 6,013,168
[45] Date of Patent: Jan. 11, 2000

[54] MICROCHIP ELECTROPHORESIS APPARATUS

[75] Inventor: Akihiro Arai, Kyoto, Japan

[73] Assignee: Shimadzu Coporation, Kyoto, Japan

[21] Appl. No.: 09/028,466

[22] Filed: Feb. 24, 1998

[30] Foreign Application Priority Data

Mar. 3, 1997 [JP] Japan ................... 9-065397

[51] Int. Cl.[7] ............................. G01N 27/26
[52] U.S. Cl. ............... 204/601; 204/602; 204/603; 422/67
[58] Field of Search ................ 204/601, 602, 204/603, 604, 606, 612, 616; 422/50, 61, 67

[56] References Cited

U.S. PATENT DOCUMENTS

| | | | |
|---|---|---|---|
| 4,810,348 | 3/1989 | Sarrine et al. | 204/612 |
| 5,045,172 | 9/1991 | Guzman | 204/603 |
| 5,124,020 | 6/1992 | Wang | 204/603 |
| 5,198,091 | 3/1993 | Burolla et al. | 204/601 |
| 5,208,466 | 5/1993 | Pentoney, Jr. | 204/602 |
| 5,372,695 | 12/1994 | Demorest | 204/602 |
| 5,384,024 | 1/1995 | Moring et al. | 204/602 |
| 5,541,420 | 7/1996 | Kambara | 204/602 |
| 5,846,395 | 12/1998 | Sarrine et al. | 204/606 |

FOREIGN PATENT DOCUMENTS

| | | |
|---|---|---|
| 581413 A2 | 2/1994 | European Pat. Off. . |
| WO 94 26396 | 11/1994 | WIPO . |

OTHER PUBLICATIONS

Document No. XP 002069051, Date Jan. 31, 1997, Country Japan, Abstract of JP 08 233 778.

Seiler K. et al., "Planar glass chips for capillary electrophoresis: repetitive sample injection, quantitation, and separation efficiency" *Analytical Chemistry*, May 1993, vol. 65, No. 10, pp. 1481–1488.

Kaltenbach P., "A high–sensitive diode array detector for on–column detection in capillary electrophoresis" *Hewlett–Packard Journal*, Jun. 1995, vol. 46, No. 3, ISSN 0018–1153, pp. 20–21.

Nakanishi H. et al., "Fabrication of electrophoresis devices on quartz and glass substrates using a bonding with HF solution" *Proceedings of the IEEE Tenth Annual International Workshop On Micro Electro Mechanical Systems*, 1997, pp. 299–304.

Primary Examiner—Robert J. Warden, Sr.
Assistant Examiner—Andrew Aldag
Attorney, Agent, or Firm—Armstrong, Westerman, Hattori, McLeland & Naughton

[57] ABSTRACT

When a microchip is set on a tray and operation of an apparatus is begun, the microchip moves to feed position in order to be filled up with a buffer solution, where upon a sample is injected into this microchip. Thereafter the tray is located on a detecting position, so that a sample introduction voltage is applied between a sample reservoir and a sample waste reservoir for introducing the sample into a separation passage. Subsequently, the operation is switched to application of a separation voltage between a buffer reservoir and a drain reservoir, for beginning analysis. When the analysis has begun, a detector detects a migration pattern in the separation passage, so that a signal processing board data-processes the detected pattern.

6 Claims, 5 Drawing Sheets

Fig. 1A PRIOR ART
Fig. 1B PRIOR ART
Fig. 1C PRIOR ART
Fig. 1D PRIOR ART
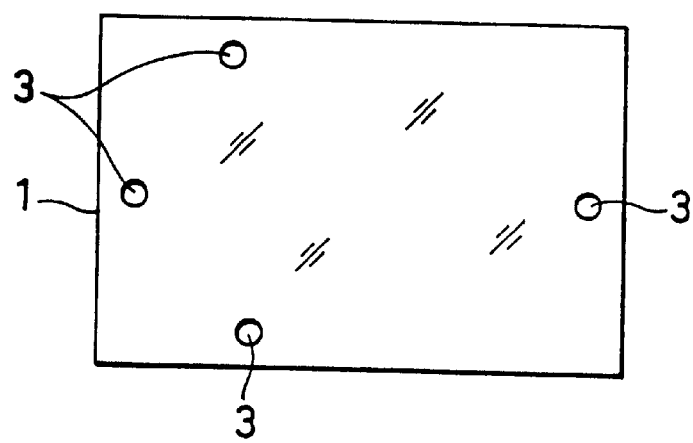
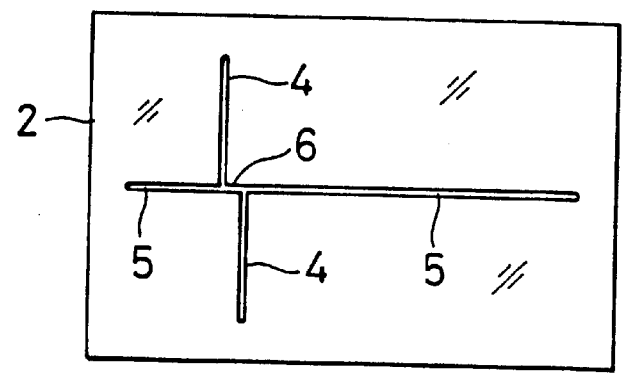
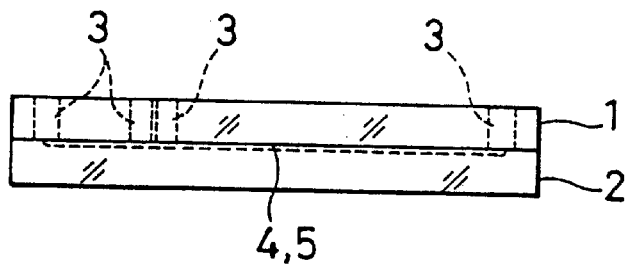
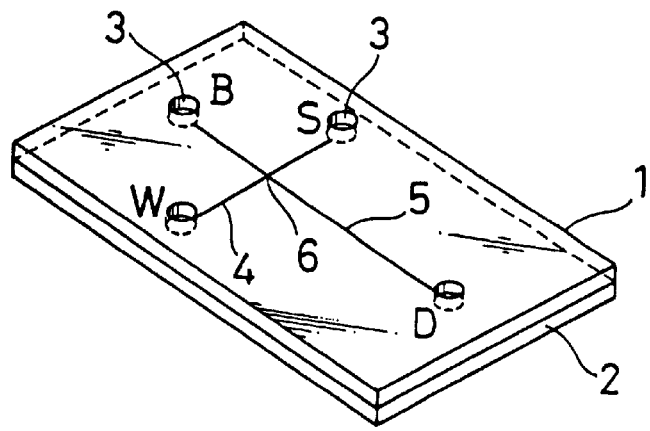

MICROCHIP ELECTROPHORESIS APPARATUS

BACKGROUND OF THE INVENTION

1. Field of the Invention

The present invention relates to an apparatus for analyzing an extremely small quantity of a wide variety of applications such as protein, nucleic acid or the like, at high speed and in high resolution. More particularly, it relates to a microchip electrophoresis apparatus employing a microchip.

2. Description of the Prior Art

A capillary electrophoresis apparatus is generally employed for analyzing an extremely small quantity of protein or nucleic acid. The capillary electrophoresis apparatus charges a glass capillary with an inner diameter of not more than 100 $\mu$m with a migration buffer, introduces a sample into an end thereof, and subsequently applies a high voltage across the glass capillary to separate molecules based on the differences in charge-to-size ratio. The capillary has a large surface area relative to its volume, (i.e., high cooling efficiency). In this way, a high voltage can be applied to the capillary for analyzing an extremely small quantity of sample, such as DNA, at a high speed in high resolution.

However, the capillary has a small outer diameter of about 100 to 400 $\mu$m, and is fragile even though it is usually protected by a polyimide coating. Therefore, the user must be extremely careful during the process of exchanging it Furthermore, the accurately measured injection of sample into a capillary is difficult, and on-capillary reaction schemes usually require junctions which are difficult or tedious to make without introducing extra volume. These have led to the proposal of a capillary electrophoretic chip (referred to as a microchip in this application) formed by connecting two substrates to each other, as described in Anal. Chim. Acta 283 (1993) pp. 361–366 by D. J. Harrison et al. FIGS. 1A to 1D show an exemplary microchip. This microchip comprises a pair of transparent substrates 1 and 2. Substrate 2 is provided with migration capillary grooves 4 and 5, which are formed by etching, which intersect each other, while substrate 1 is provided with through holes 3 in positions corresponding to both ends of grooves 4 and 5.

When employing this microchip, substrate 1 and 2 are superimposed over one another as shown in FIGS. 1 C and 1 D, so that an electrolyte or an electrophoretic buffer solution (hereinafter refer to as "buffer solution") may be injected into grooves 4 and 5 from any through hole 3. Following this, thereafter a sample is injected from through hole 3(S), which is located at one end of shorter groove 4, and a high voltage is then applied between through holes 3(S) and 3(W), which are located at both ends of groove 4, for a prescribed time. In this way, the sample is dispersed in groove 4.

Following this, a separation voltage for electrophoretic separation is applied between through holes 3(B) and 3(D), which are located at both ends of longer groove 5. Thus, the sample which is present on intersection 6, between grooves 4 and 5, is electrophoresed in groove 5. A detector, such as an ultraviolet-visible spectrophotometer, a fluorophotometer, or an electrochemical detector, is located in a position relative to groove 5 in order to detect the separated component It has been demonstrated that such electrophoresis with a microchip is capable of high-speed separation and microanalysis in miniaturized system. If instrumentation of the electrophoresis progresses, there is the potential of attaining a completely new and unique analyzer.

In the aforementioned technique employing the microchip, the buffer solution is manually charged in grooves 4 and 5 from any through hole 3. The sample is also manually injected into through hole 3(S). Through hole 3, which is used for the buffer solution, serves as a reservoir for the buffer solution, and through hole 3(S), for injecting the sample, acts as a sample container. Pre-analytical operations entail manually feeding the buffer solution into any through hole 3 with a syringe or similar instrument, and injecting the sample into through hole 3(S), which is provided on one end of groove 4, with another syringe.

FIG. 2 shows an exemplary electrophoresis apparatus employing a microchip 10.

X-Y stage 12 is placed on optical bench 14 as a mechanism for moving microchip 10 in a horizontal plane. Microchip 10 is attached to X-Y stage 12 and manually moved in the horizontal plane along directions X and Y. A laser induced fluorescence detector, which excites a given sample by means of laser beam for detecting it through its fluorescence emission, optically detects the sample separated by electrophoresis in a migration passage. The laser beam from laser unit 16 is passed into a confocal microscope 18 and reflected with a dichroic mirror to an objective, which focused the sample injected into microchip 10. The fluorescence generated from the sample is collected by the same objective, passed through the dichroic mirror, filtered by a bandpass filter and focesed on a pinhole followed by photomultiplier 20 detection. Binocular 22 adjusts the optical axis of the irradiating and condensing part 18. Laser unit 16, confocal microscope 18 and binocular 22 are also arranged on optical bench 14. Numeral 24 denotes a laser power source, while numeral 26 denotes a high-voltage power source for photomultiplier 20. Amplifier 28 amplifies an optical signal detected by photomultiplier 20, and A-D converter 30 converts the amplified signal to a digital signal, so that CPU 32 is able to retrieve this digital signal.

High-voltage power sources 34 and 36 are provided for applying a sample introduction voltage to introduce the sample, which is injected into microchip 10, into a separation passage and a separation voltage for electrophoretically separating the sample respectively. High-voltage power sources 34 and 36 apply the voltages to microchip 10 through relay control system 38. CPU 32 serves as a control unit, switching the sample introduction voltage and the separation voltage through relay control system 38, and collecting data from A-D converter 30 prior to processing it CPU 32 is connected to external personal computer 39 for transmittng and receiving the data.

In the electrophoresis apparatus shown in FIG. 2, the buffer solution must be introduced into the passage of microchip 10 with a syringe or similar instrument, and the sample of several $\mu$l must also be introduced into sample reservoir S, by similar means before microchip 10 is set on X-Y stage 12. The laser beam must be focused on a point of the separation passage in order to detect the electrophoretically separated sample. The optical alignment of the system is made visually using a three-axis translation stage with respect to a fixed microscope.

This electrophoresis apparatus requires a preliminary operation of the filling up of microchip 10 with the buffer solution and subsequent positioning of the sample on sample reservoir S. Additionally, the optical axis of the laser beam must be adjusted to the separation passage of microchip 10 which requires the strict alignment of microchip 10 with the detector in order to efficiently condense the fluorescence. Therefore, large-scale devices such as binocular 22, optical bench 14, an optical axis adjusting mechanism, general-purpose high-voltage power sources 34 and 36, laser unit 16 and power source 24 are required, although microchip 10, itself, is relatively small (something in the region of 20 mm by 40 mm,), and is employed for microanalysis which hardly consumes a reagent

SUMMARY OF THE INVENTION

The purpose of the present invention is to enable automatic treatments (such as the charging of a buffer solution, sample injection, sample introduction into a separation passage, separation by electrophoresis and detection subsequent to setting a microchip on a prescribed position) by an apparatus which stores its respective parts in a compact, integrated unit.

The present invention is a microchip electrophoresis apparatus which employs a microchip provided with a separation passage and a sample introduction passage which intersect one another. The apparatus also comprises a detector for optically detecting an electrophoretically separated sample, a mechanism for moving the microchip which is horizontally positioned on a tray, a liquid injection mechanism for injecting a buffer solution into the passages from a through hole of the microchip, a sample injection mechanism for injecting a sample from a sample injection hole of a through hole located at one end of the sample introduction passage, a power source for switching and applying a sample introduction voltage for introducing the sample into the separation passage from the sample introduction passage and a separation voltage for electrophoretically separating the sample. It further comprises a CPU board which automatically controls the movement of the microchip by means of a mechanism which locates it on a series of positions which include: a buffer solution injecting position via the liquid injection mechanism, a sample injecting position via the sample injection mechanism and a detecting position via the detector. The CPU board further controls the operations of the liquid injection mechanism and the sample injection mechanism, along with the application of the sample introduction voltage and the separation voltage by the power source. The microchip electrophoresis apparatus is housed in a case, which integrally stores all of these parts.

In the present invention, the parts necessary for microchip electrophoretic analysis are integrated with each other and an analytical sequence is automatized, thereby reducing the time of analysis and increasing accuracy.

Furthermore, the apparatus is portable, and, when applied to a dedicated apparatus using a fixed detection wavelength employed in a fixed field, leads to size reduction of the detector, which in turn influences the size of the overall apparatus.

The detector and the mechanism for moving the microchip which has been placed on the tray are integrated with each other, allowing for optical axis adjustment of the passages of the microchip to be stabilized.

After setting the microchip on the tray, it is possible to automatically charge the buffer solution in the passages, introduce the sample into the separation passage and move the microchip to the detecting position whereby voltage may be applied for analysis.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1A is a plan view showing a substrate provided with through holes forming an exemplary microchip employed both in a conventional apparatus and in an apparatus according to the present invention. FIG. 1B is a plan view showing another substrate provided with grooves forming the microchip, and FIGS. 1C and 1D are a front elevational view and a perspective view of the microchip respectively.

DESCRIPTION OF THE PREFERRED EMBODIMENTS

Figure 2:
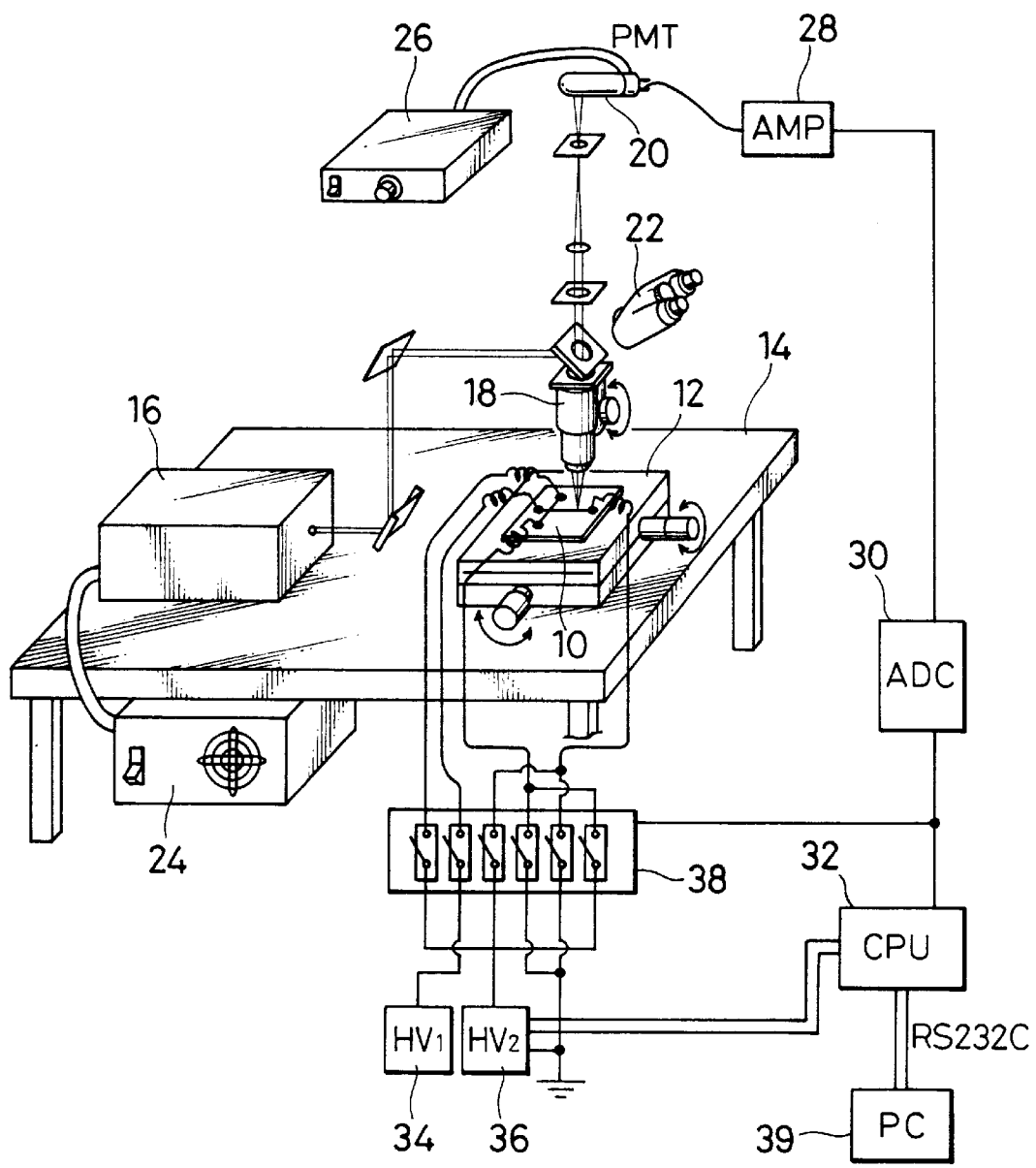
FIG. 2 is a schematic perspective view showing a conventional microchip electrophoresis apparatus.
Figure 3:
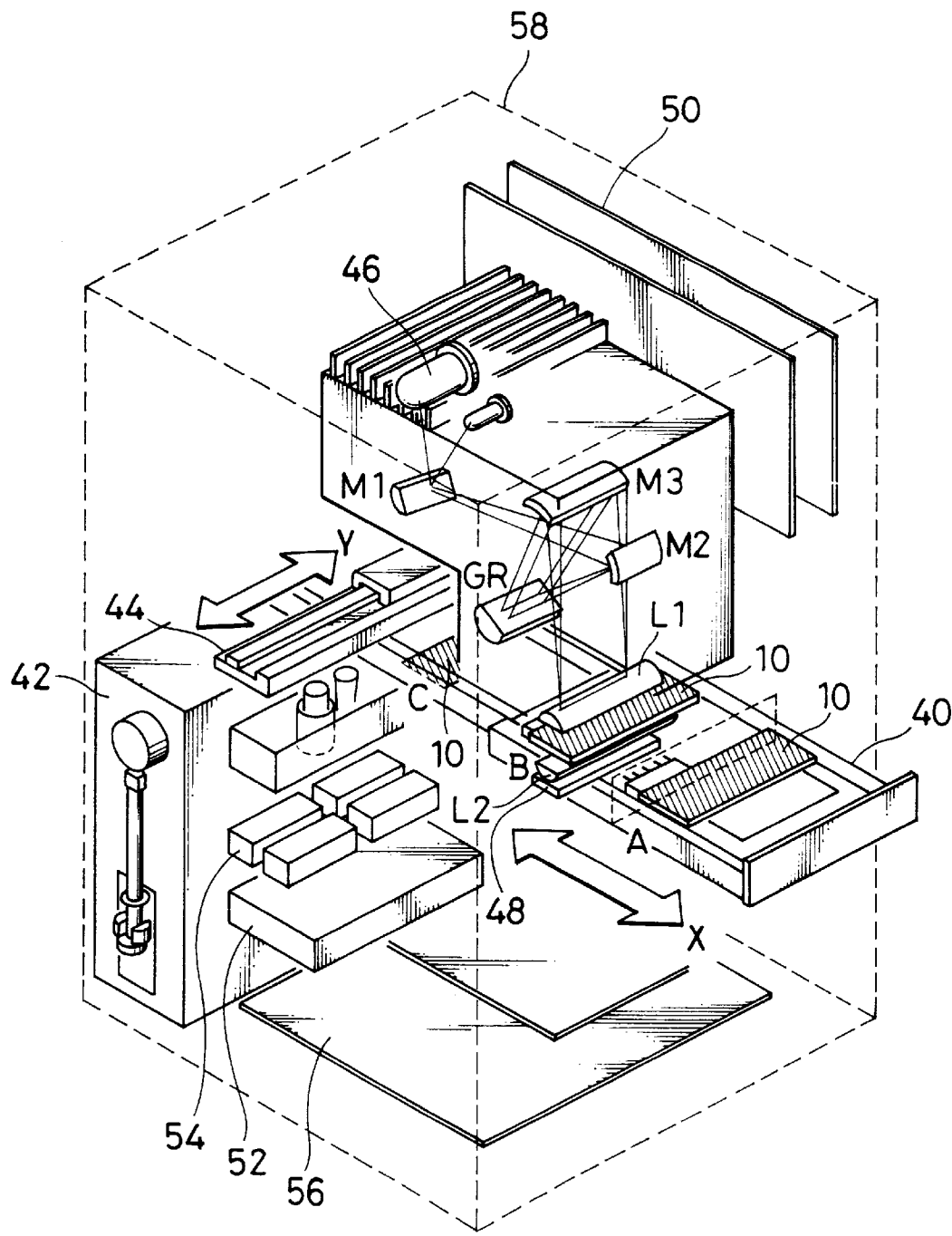
FIG. 3 is a schematic perspective view showing the internal structure of a microchip electrophoresis apparatus according to an embodiment of the present invention.
Figure 4:
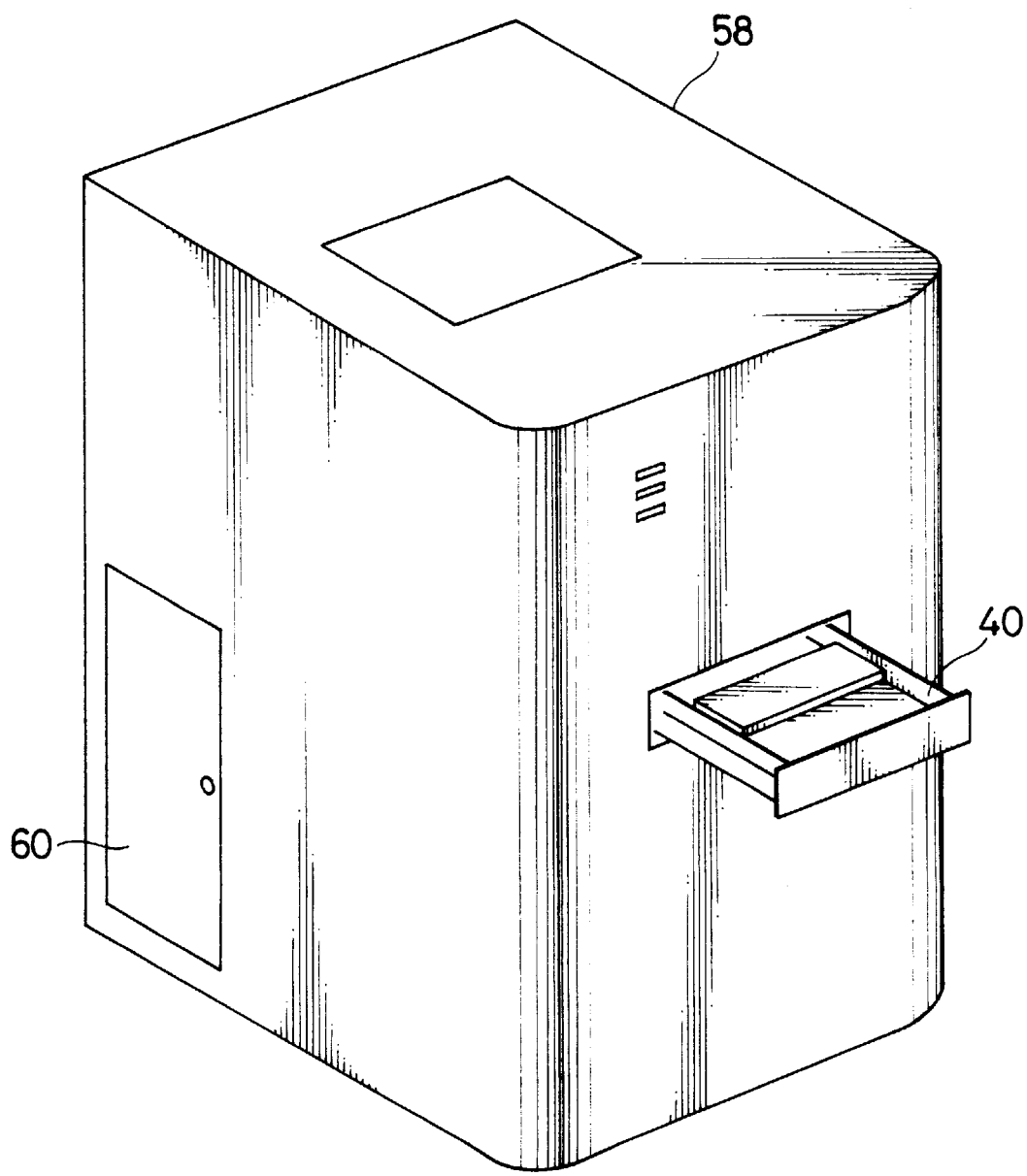
FIG. 4 is a perspective view showing the storage case which houses the parts of the embodiment

FIG. 3 is a schematic perspective view showing the internal structure of a microchip electrophoresis apparatus according to an embodiment of the present invention, and FIG. 4 is a perspective view showing the storage case which houses same.

Microchip 10, which is identical to that shown in FIGS. 1A to 1D, is made of glass, quartz or resin, the surface of which is provided with electrode patterns connecting to passages via through holes 3. The electrode patterns, which are formed by vapor deposition, are connected to a terminal.

Tray 40, which is provided as a moving mechanism for fixing microchip 10 and moving same in a horizontal plane, can move in directions X and Y for locating microchip 10 on prescribed positions.

Tray 40 locates microchip 10 on setting position A for connecting the voltage terminal of microchip 10 with a connector of the apparatus. This connector is connected to a power source for applying a sample introduction voltage and a separation voltage for electrophoretic separation. The power source applies the sample introduction voltage and the separation voltage to the passages through the connector, the voltage terminal and the electrode patterns and through holes 3 of microchip 10.

Optical axis adjustment is carried out on optical detecting position B.

Syringe unit 42, serving both as an liquid injection mechanism and a sample injection mechanism, injects a buffer solution and a sample on position C. Microchip 10 is moved in the direction Y to a position for aligning a reservoir, cleaning a syringe and discharging the solution. The apparatus is further provided with a mechanism for moving tray 40 in the direction X and a mechanism for moving it in the direction Y along guide 44, although these mechanisms are not illustrated.

The apparatus employs a spectrophotometric detector as a detector. The detector employs $D_2$ lamp 46 as a light source, and mirrors $M_1$ and $M_2$ reflect light from lamp 46 to grating GR, which separates this light into its spectral components. Cylindrical lens $L_1$ linearly condenses the separated light and irradiates a separation passage of microchip 10 located on position B with this light from grating GR through mirror $M_3$. Cylindrical lens $L_2$, provided on the opposite side, condenses the light transmitted through microchip 10, and silicon photodiode array 48 detects the condensed light Silicon photodiode array 48 is adapted to simultaneously receive the light transmitted through a prescribed range of the separation passage in order to detect its migration pattern. A detection signal of silicon photodiode array 48 is transmitted to and processed in signal processing board 50.

Syringe unit 42, which serves as both the liquid injection mechanism for injecting a buffer solution from any through hole of microchip 10, and the sample injection mechanism for injecting a sample from the sample injection hole of the through hole positioned on an end of the sample introduction passage of microchip 10, charges the buffer solution and injects the sample into microchip 10 located on position C.

High-voltage power source 52 and high-voltage relay 54, which switches the voltage applied to microchip 10 and a current passage, are provided as power sources for switching and applying a sample introduction voltage for introducing the sample which is injected into the sample introduction passage of microchip 10, into the separation passage, and a separation voltage for electrophoretically separating the sample respectively.

Control part 56 takes the form of a CPU board. Control part 56 controls microchip 10 with tray 40 of the moving mechanism which locates microchip 10 on a buffer solution injecting position, a sample injecting position and a detecting position. It also controls the buffer solution injecting operation, a sample injecting operation with syringe unit 42, along with the voltage application by high-voltage power source 52 and high-voltage relay 54.

These parts are integrated with each other as shown in FIG. 3, and stored in case 58 as shown in FIG. 4. Tray 40 can be accessed by means of a window positioned on the front surface of case 58. When tray 40 projects from the window, setting position A is exposed to the exterior of case 58, enabling the setting or removal of microchip 10. The supply and exchange of the buffer solution and the sample takes place in syringe unit 42, through door 60.

Figure 5:
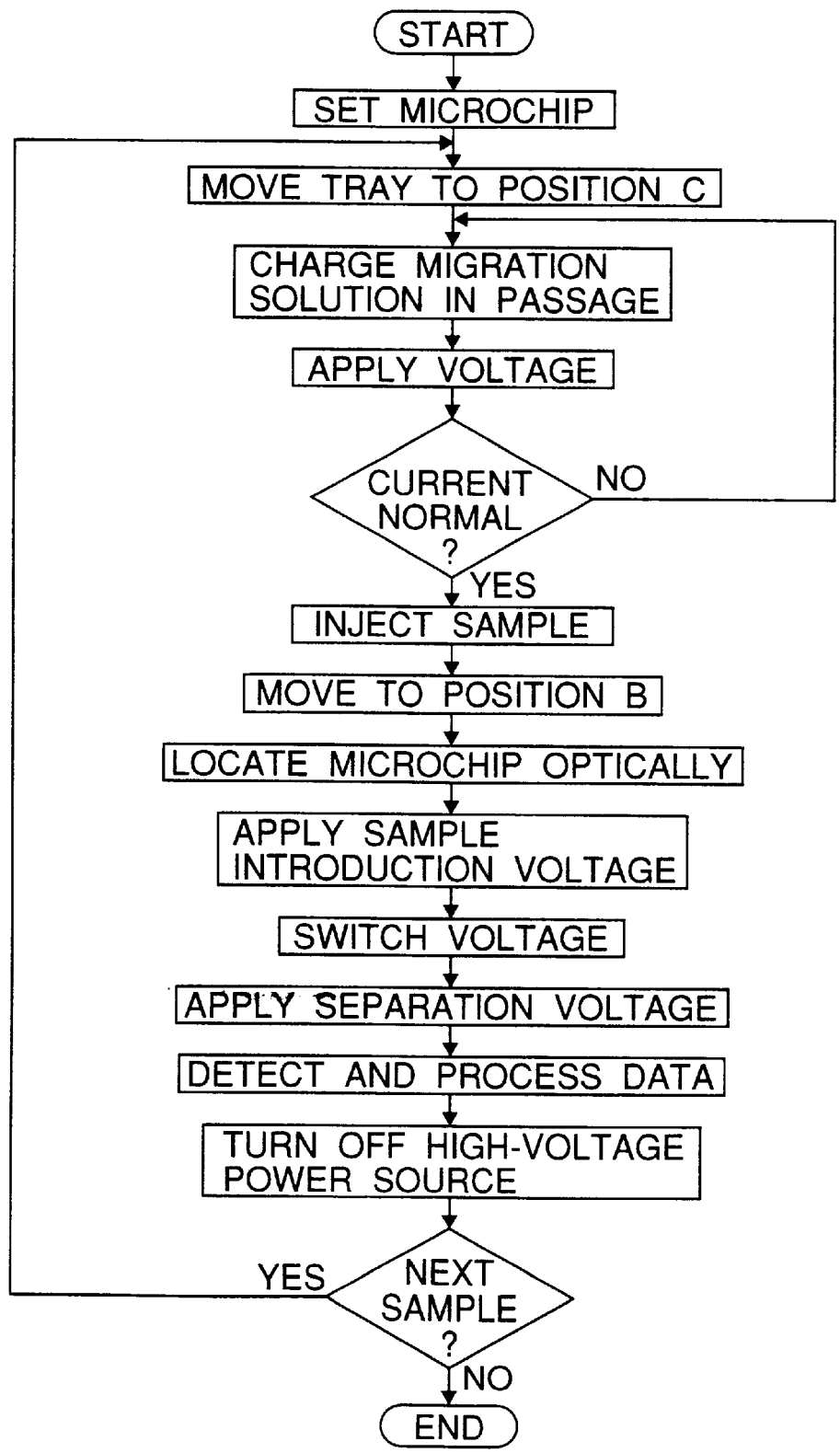
FIG. 5 is a flow chart showing the operation of the embodiment

The operation of the microchip electrophoresis apparatus according to this embodiment is now described with reference to a flow chart shown in FIG. 5. When microchip 10 is set on tray 40 and operation of the apparatus is begun, tray 40 moves to position C. A rod which has a discharge port for the buffer solution then moves in the direction Y, perpendicularly to the movement of tray 40 which travels in direction X in order to charge the buffer solution in the passages of microchip 10. Syringe unit 42, which is integrated into the apparatus, supplies the buffer solution.

Subsequently, tray 40 temporarily moves to an arbitrary position, displaced from position C, between positions B and C, whereupon control part 56 applies a voltage of about 0.5 kV across the passages of microchip 10. Control part 56 then monitors this current, confirms its stability and checks that the buffer solution is properly filled. If no current value is measured, or the current is unstable, control part 56 determines that the buffer solution is not properly filled or bubbles are formed within the passage, returns microchip 10 to position C, repeats the process of charging the buffer solution, and once again determines whether or not the buffer solution has been properly filled.

After determining that the buffer solution is properly filled, control part 56 returns microchip 10 to position C and moves a needle for injecting the sample into sample reservoir S in the direction Y. In this case, syringe unit 42, which is integrated into the apparatus, also supplies the sample.

After injection of the sample, tray 40 slowly moves through detecting position B. At this time, control unit 56 monitors the signal from the detector. When a beam strikes the surfaces of the passages, scattered light is generated and hence background illumination increases. Control part 56 controls the movements of tray 40 ensuring that microchip 10 comes to be located at an intermediate position between two peaks.

Control part 56 applies the sample introduction voltage between sample reservoir S and a sample waste reservoir W after locating microchip 10 on the detecting position B, and then switches to application of the electrophoretic separation voltage between buffer reservoir B and drain reservoir D to begin analysis.

When analysis has begun, the detector detects a migration pattern in the separation passage, and signal-processing board 50 data-processes the detected pattern. When analysis of a single sample is complete, control part 56 stops application of the electrophoretic separation voltage.

When repeated analysis is necessary, control part 56 moves microchip 10 away from detecting position B to position C, washes away the sample left in the passages with the buffer solution, injects the next sample, and repeats the aforementioned operation.

Control part 56 stores this series of operations as a program, for automatically executing it As described above, even if the positional accuracy of the mechanism used for moving the microchip is insufficient, it is possible to automatically locate the microchip on the detecting position providing that location resolution is ensured. This is accomplished by setting the microchip so that the separation passage is perpendicular to the directional movement of the microchip and feeding back the signal outputted from the detector when its optical axis crosses the separation passage for the microchip to the mechanism determining the movements of the microchip.

If the positional accuracy of the mechanism for moving the microchip is sufficient, location of the microchip through the signal from the detector can be omitted.

Although the present invention has been described and illustrated in detail, it must be clearly understood that this is by way of illustration and example only, and should not be seen in terms of limitation. The spirit and scope of the present invention is limited only by the terms of the appended claims.

What is claimed is:

1. A microchip electrophoresis apparatus employing a microchip comprising a pair of transparent plate members, a groove formed on a surface of at least one said plate member for passing a liquid therethrough and through holes provided on any one said plate member in positions corresponding to both ends of said groove, said plate members being stuck to each other while inwardly directing said groove for defining a separation passage and a sample introduction passage intersecting with each other by said groove, for filling up said separation passage and said sample introduction passage with a buffer solution, applying a sample introduction voltage across said sample introduction passage and introducing a sample from said sample introduction passage into said separation passage, and subsequently applying a separation voltage across said separation passage for electrophoretically separating said sample in said separation passage, said microchip electrophoresis apparatus comprising:

a detector for optically detecting electrophoretically separated said sample;

a moving mechanism for moving said microchip, which is horizontally positioned on a tray;

a liquid injection mechanism for injecting said buffer solution from said through holes;

a sample injection mechanism for injecting said sample from a sample injection hole of said through hole positioned on an end of said sample introduction passage;

a power source for switching and applying a sample introduction voltage for introducing said sample from said sample introduction passage into said separation passage and a separation voltage for electrophoretically separating said sample;

a control part for automatically controlling the movement of said microchip by means of said moving mechanism for locating said microchip on a series of positions which include; a buffer solution injecting position with said liquid injection mechanism; a sample injecting position with said sample injection mechanism and a detecting position with said detector respectively; said control part further controlling operations of said liquid injection mechanism and said sample injection mechanism and control of voltage application with said power source; wherein said control part comprises a program for applying a prescribed voltage across said passages of said microchip after said passages are filled up with said buffer solution and which then determines whether or not said passages are properly filled up with said buffer solution upon determining the presence of a current value; and a case which integrally stores all these parts.

2. The microchip electrophoresis apparatus in accordance with claim 1, wherein said transparent plate members of said microchip are made of glass, quartz or resin, electrode patterns connecting to said separation passage and said sample introduction passage through which said through holes are formed on one of said transparent plate members, and said electrode patterns connect to a voltage terminal, and said voltage terminal is connected to a connector which is connected to said power source, thereby applying said sample introduction voltage and said separation voltage to said passages through said electrode patterns.

3. The microchip electrophoresis apparatus in accordance with claim 1, wherein said detector is a spectrophotometric detector, comprising a spectroscope for separating light from a light source into its spectral components, an optical system for linearly condensing separated said light on said separation passage of said microchip which is located on said detecting position and irradiating said separation passage with said light, and arrayed photodetectors for simultaneously receiving light transmitted through a prescribed range of said separation passage and detecting its migration pattern.

4. The microchip electrophoresis apparatus in accordance with claim 1, wherein said case is provided with a window on its front surface which is capable of partially exposing said tray for enabling the setting or removal of said microchip in respect to said tray.

5. The microchip electrophoresis apparatus in accordance with claim 1, wherein said control part also comprises a program for re-locating said microchip on said buffer solution injecting position for re-filling said passages with said buffer solution upon determining that said passages have not been properly filled up with said buffer solution.

6. The microchip electrophoresis apparatus in accordance with claim 1, wherein said microchip is so arranged that said separation passage is perpendicular to the directional movement of said microchip when moved to said detecting position with said detector, and said control part feeds back a signal outputted from said detector when an optical axis of said detector crosses said separation passage of said microchip to said moving mechanism which moves said microchip thereby locating said microchip on said detecting position.

* * * * *